US 6,526,123 B2

(12) United States Patent
Ein-Gal

(10) Patent No.: US 6,526,123 B2
(45) Date of Patent: *Feb. 25, 2003

(54) MULTIPLE LAYER MULTILEAF COLLIMATOR

(76) Inventor: Moshe Ein-Gal, Azar Street 30, 47203 Ramat Hasharon (IL)

(*) Notice: Subject to any disclaimer, the term of this patent is extended or adjusted under 35 U.S.C. 154(b) by 0 days.

This patent is subject to a terminal disclaimer.

(21) Appl. No.: 09/891,659

(22) Filed: Jul. 6, 2001

(65) Prior Publication Data
US 2001/0043669 A1 Nov. 22, 2001

Related U.S. Application Data

(63) Continuation of application No. 09/308,088, filed as application No. PCT/IL98/00473 on Sep. 28, 1998, now Pat. No. 6,266,393.

(30) Foreign Application Priority Data

Sep. 29, 1997 (IL) .................................................. 121866

(51) Int. Cl.[7] .................................................. G21K 1/04
(52) U.S. Cl. ........................ 378/152; 378/65; 378/147; 250/505.1
(58) Field of Search ................................ 378/147, 150, 378/152, 64, 65, 138; 250/505.1

(56) References Cited

U.S. PATENT DOCUMENTS

| 4,987,309 | A | * | 1/1991 | Klasen et al. | 250/492.1 |
| 5,591,983 | A | * | 1/1997 | Yao | 250/505.1 |
| 5,748,703 | A | * | 5/1998 | Cosman | 378/152 |
| 5,889,834 | A | * | 3/1999 | Vilsmeier et al. | 378/147 |
| 6,266,393 | B1 | * | 7/2001 | Ein-Gal | 378/152 |

* cited by examiner

Primary Examiner—Drew A. Dunn
Assistant Examiner—Allen C Ho
(74) Attorney, Agent, or Firm—David Klein; Dekel Patent Ltd.

(57) ABSTRACT

A multileaf collimator for use in a radiation system providing a radiation beam in a given beam direction, including a first layer of a plurality of radiation blocking leaves, the leaves being arranged adjacent one another so as to form two opposed rows of adjacently positioned leaves and being movable in a longitudinal direction (Y) which is generally transverse to the beam direction, defining a radiation beam shaping field between the opposed ends of the leaves, a second layer of a plurality of radiation blocking leave, the leaves of the second layer being arraigned adjacent one another as to form two opposed rows of adjacently positioned leaves and being movable in a cross-over direction (X) which is generally transverse to the beam direction and angled with respect to the longitudinal direction (Y), defining a radiation beam shaping field between the opposed ends of the leaves of the second layer.

10 Claims, 5 Drawing Sheets

MULTIPLE LAYER MULTILEAF COLLIMATOR

FIELD OF THE INVENTION

The present invention relates generally to a multiple layer multileaf collimator for use during radiation treatment to shape and control the spatial distribution of a radiation beam.

BACKGROUND OF THE INVENTION

During conventional radiation therapy treatment, radiation beams of varying angles and intensities are directed at a target in a patient. Normal tissue and organs located in the path of the radiation beams must be taken into account for safety reasons, thereby limiting the dose that can be delivered to the target. Many techniques are known for shaping the radiation beams so that the radiation is concentrated at the target and is minimized or eliminated at the normal tissues. One of the techniques is conformal radiation therapy wherein the beam aperture varies from angle to angle via a multileaf collimator which employs a multiplicity of radiation blockers, called leaves. Each individual leaf in a multileaf collimator can be positioned independently, allowing the user to create an infinite amount of irregularly shaped fields. The radiation beams are directed between the ends of opposing arrays of the radiation blocking collimator leaves, thereby shaping the beam to closely match the shape of the desired treatment area, while shielding the normal tissue and organs.

An example of such a system is U.S. Pat. No. 5,166,531 to Huntzinger which describes a multileaf collimator arrangement positioned about the central axis of a radiation emitting head for shaping an emitted radiation beam. The collimator includes two opposing arrays of side-by-side elongated radiation blocking collimator leaves. Each leaf in each opposing array can be moved longitudinally towards or away from the central axis of the beam, thus defining a desired shape through which the radiation beam will pass. However, because the adjoining leaves must be tightly positioned side-by-side in order to minimize radiation leakage between the leaves, friction is an inherent problem, creating complications in maintaining a set position of one leaf while re-positioning an adjacent leaf such repositioning being frequently required in conformal therapy. If friction between the adjacent leaves is reduced by providing a looser fit between adjacent leaves, unacceptable radiation leakage through spaces between the adjacent leaves will result. On the other hand, maintaining a tight leaf fit between the adjacent leaves and providing a lubricating layer in the contact area of the adjacent leaves is also not an acceptable solution because the lower density of the lubricating layer, as compared to the high density of the collimator leaves, will allow an unacceptable amount of radiation leakage to occur.

U.S. Pat. No. 5,591,983 to Yao, the disclosure of which is incorporated herein by reference, attempts to solve the friction problem by providing a collimator that comprises first and second layers of a plurality of elongated radiation blocking leaves. The leaves of each layer are arranged adjacent one another so as to form two opposed rows of adjacently positioned leaves and are movable in a longitudinal direction (Y) which is generally traverse to the direction of the beam so as to define a radiation beam shaping field between the opposed ends of the leaves. The layers are arranged one above another in the beam direction and offset in a lateral direction (X) generally transverse to the beam direction and orthogonal to the longitudinal direction (Y) so that spaces between adjacent leaves of the first and second layers are positioned over and under, respectively, leaves of the second and first layers, respectively.

One disadvantage of the Yao system is that an irregularly shaped target is poorly covered by the two layers of leaves. In addition, the overall thickness of the leaves in the beam direction is quite large.

Other patent documents related to multileaf collimators include U.S. Pat. No. 4,233,519 to Coad, U.S. Pat. No. 4,534,052 to Milcamps, U.S. Pat. No. 4,672,212 to Brahme, U.S. Pat. No. 4,739,173 to Blosser et al., U.S. Pat. No. 4,754,147 to Maughan et al., U.S. Pat. No. 4,794,629 to Pastyr et al., U.S. Pat. No. 4,868,843 and U.S. Pat. No. 4,868,844 to Nunan, U.S. Pat. No. 5,012,506 to Span et al., U.S. Pat. No. 5,165,106 to Barthelmes et al., U.S. Pat. No. 5,207,223 to Adler, U.S. Pat. No. 5,343,048 to Pastyr, U.S. Pat. No. 5,351,280 to Swerdloff et al., U.S. Pat. No. 5,427,097 to Depp, U.S. Pat. No. 5,438,991 to Yu et al., U.S. Pat. No. 5,442,675 to Swerdloff et al., and U.S. Pat. No. 5,555,283 to Shiu et al.

SUMMARY OF THE INVENTION

The present invention seeks to provide a multiple layer multileaf collimator with non-parallel layers that cross over each other. For example, a first layer employs radiation blocking leaves that are movable in a longitudinal direction (Y) which is generally traverse to the direction of the beam so as to define a radiation beam shaping field between the opposed ends of the leaves. A second layer of leaves positioned above the first layer employs radiation blocking leaves that are movable in a cross-over direction (X) which is generally traverse to the direction of the beam so as to define a radiation beam shaping field between the opposed ends of the leaves, the cross-over direction (X) being generally orthogonal to longitudinal direction (Y). Alternatively, the first and second layers can be angled with respect to each other at an angle other than 90°, Although gaps in the X-Y plane are formed between the crossed-over layers, these gaps are sufficiently small so as to pass a negligibly safe amount of radiation. Unlike the prior art, any irregularly shaped target can be accurately covered by the two layers of leaves. In addition, the overall thickness of the leaves in the beam direction is significantly less than the prior art.

There is thus provided in accordance with a preferred embodiment of the present invention a multileaf collimator for use in a radiation system providing a radiation beam in a given beam direction, including a first layer of a plurality of radiation blocking leaves, the leaves being arranged adjacent one another so as to form two opposed rows of adjacently positioned leaves and being movable in a longitudinal direction (Y) which is generally traverse to the beam direction so as to define a radiation beam shaping field between the opposed ends of the leaves, a second layer of a plurality of radiation blocking leaves, the leaves of the second layer being arranged adjacent one another so as to form two opposed rows of adjacently positioned leaves and being movable in a cross-over direction (X) which is generally traverse to the beam direction and angled with respect to the longitudinal direction (Y) so as to define a radiation beam shaping field between the opposed ends of the leaves of the second layer, and actuator apparatus for moving the leaves of the first layer in the longitudinal direction (Y) and the leaves of the second layer in the cross-over direction (X), wherein the first and second layers are arranged one above another in an overlapping manner in the beam direction.

In accordance with a preferred embodiment of the present invention gaps are formed generally traverse to the beam direction and generally in a plane of the X and Y directions, each of the gaps only allowing an amount of radiation to pass therethrough below a predetermined threshold.

Further in accordance with a preferred embodiment of the present invention the cross-over direction is generally orthogonal to the longitudinal direction.

Still further in accordance with a preferred embodiment of the present invention the leaves of the first layer and the leaves of the second layer are housed in a frame.

Additionally in accordance with a preferred embodiment of the present invention there is provided a source of radiation for providing a radiation beam in the given beam direction. Imaging apparatus may also be provided for imaging a target irradiated by the radiation beam.

In accordance with a preferred embodiment of the present invention an optical control device is provided that monitors travel of any of the leaves and signals the actuator apparatus to stop moving the leaves.

The multileaf collimator may include a plurality of the first layers of radiation blocking leaves and/or a plurality of the second layers of radiation blocking leaves.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
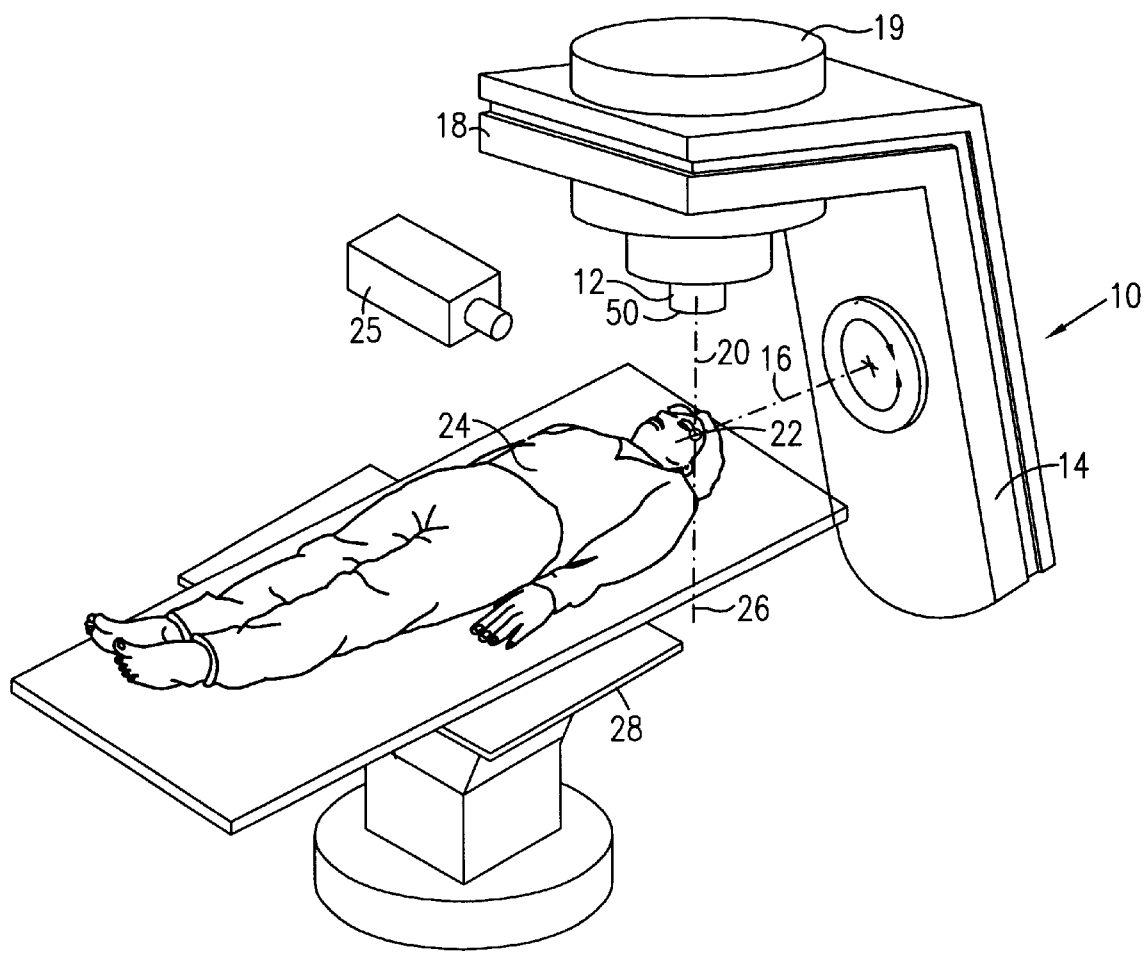
FIG. 1 is a simplified pictorial illustration of a radiation system constructed and operative in accordance with a preferred embodiment of the present invention.

Reference is now made to FIG. 1 which illustrates a radiation system 10 in which a multileaf collimator 12, constructed and operative in accordance with a preferred embodiment of the present invention, is installed. Radiation system 10 is illustrated as having a conventional LINAC gantry design, but it is appreciated that the multileaf collimator of the present invention is applicable to any radiation system design, such as the system of applicant/assignee's U.S. patent application Ser. No. 08/753,822, the disclosure of which is incorporated herein by reference. Radiation system 10 includes a gantry 14 which can be rotated about a horizontal axis 16 in the course of a therapeutic treatment. Collimator 12 is fastened to an extension 18 of gantry 14. Extension 18 includes a source of radiation 19, such as a linear accelerator, for generating a radiation beam 20 which is emitted from a central axis of radiation system 10 which is coincident with a central axis of collimator 12. Any radiation may be used, such as electron radiation or photon radiation (gamma radiation). During treatment, beam 20 is trained on a target in a patient 24 to be treated and which lies in the isocenter 22 of the gantry rotation. Axis 16 of gantry 14, an azimuthal rotational axis 26 of a treatment table 28 and beam 20 all intersect at the isocenter 22.

Imaging apparatus 25, such as a fluoroscope or ultrasound apparatus, for example, is preferably provided for imaging the target irradiated by radiation beam 20. Imaging apparatus 25, inter alia, may be used in conjunction with a closed loop, feedback control system (not shown) for controlling a position of gantry 14 and for controlling the functioning of collimator 12.

Figure 2:
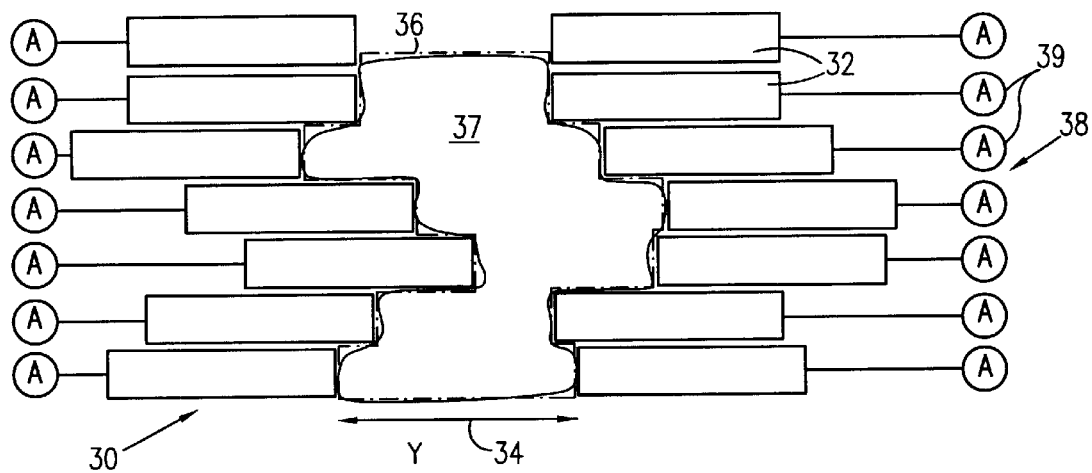
FIG. 2 is a simplified top view illustration of a first layer of a plurality of radiation blocking leaves of a multileaf collimator of the radiation system of FIG. 1, constructed and operative in accordance with a preferred embodiment of the present invention.

Reference is now made to FIG. 2 which illustrates (in a top view) a first layer 30 of a plurality of radiation blocking leaves 32 of multileaf collimator 12, constructed and operative in accordance with a preferred embodiment of the present invention. Leaves 32 are arranged adjacent one another so as to form two opposed rows of adjacently positioned leaves movable in a longitudinal direction (Y) 34 which is generally traverse to the direction of beam 20, i.e., pointing perpendicularly to the plane of FIG. 1, so as to define a radiation beam shaping field 36, shown in phantom outline, between the opposed ends of the leaves 32.

Actuator apparatus 38 is provided for moving leaves 32 in longitudinal direction 34 so as to controllably define radiation beam shaping field 36. Actuator apparatus 38 preferably includes an actuator 39 dedicated for each leaf 32. An example of actuator 39 is an individually driven worm gear for individually engaging a toothed track or floating nut mounted on each leaf 32, such as the prior art leaf driving means described in U.S. Pat. No. 5,160,847 to Leavitt et al., the disclosure of which is incorporated herein by reference. Radiation beam shaping field 36 is tailored to fit as closely as possible to the shape of a target 37 to be irradiated.

Figure 3:
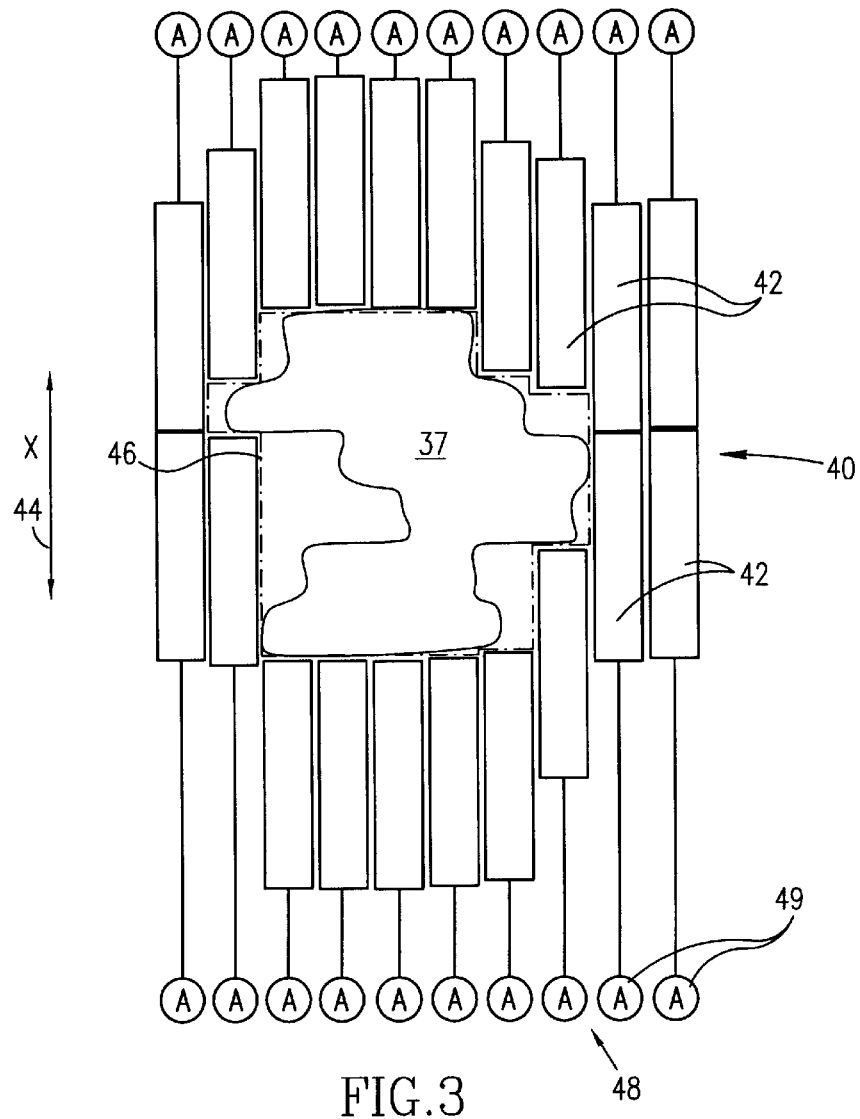
FIG. 3 is a simplified top view illustration of a second layer of a plurality of radiation blocking leaves of the multileaf collimator of the radiation system of FIG. 1.

Reference is now made to FIG. 3 which similarly illustrates (in a top view) a second layer 40 of a plurality of radiation blocking leaves 42 of multileaf collimator 12, constructed and operative in accordance with a preferred embodiment of the present invention. Leaves 42 are arranged adjacent one another so as to form two opposed rows of adjacently positioned leaves movable in a cross-over direction (X) 44 which is generally traverse to the direction of beam 20, i.e., pointing perpendicularly to the plane of FIG. 1, so as to define a radiation beam shaping field 46, shown in phantom outline, between the opposed ends of the leaves 42. Cross-over direction 44 is shown in FIG. 3 as being generally orthogonal to longitudinal direction 34, however, cross-over direction 44 may make any arbitrary angle with longitudinal direction 34 other than 90°.

Actuator apparatus 48 is provided for moving leaves 42 in cross-over direction 44 so as to controllably define radiation beam shaping field 46. Actuator apparatus 48 preferably includes an actuator 49 dedicated for each leaf 42, as described hereinabove for actuator apparatus 38. Radiation beam shaping field 46 is tailored to fit as closely as possible to the shape of target 37. However, it can be seen in FIG. 3 that the irregular shape of target 37 is poorly covered by leaves 42 alone, which is one of the drawbacks of the prior art systems such as that of U.S. Pat. No. 5,591,983. As will be described with reference to FIG. 5, an advantage of the present invention is that the overlapping of layers 30 and 40 helps to improve the resolution of coverage of target 37.

Figure 4:
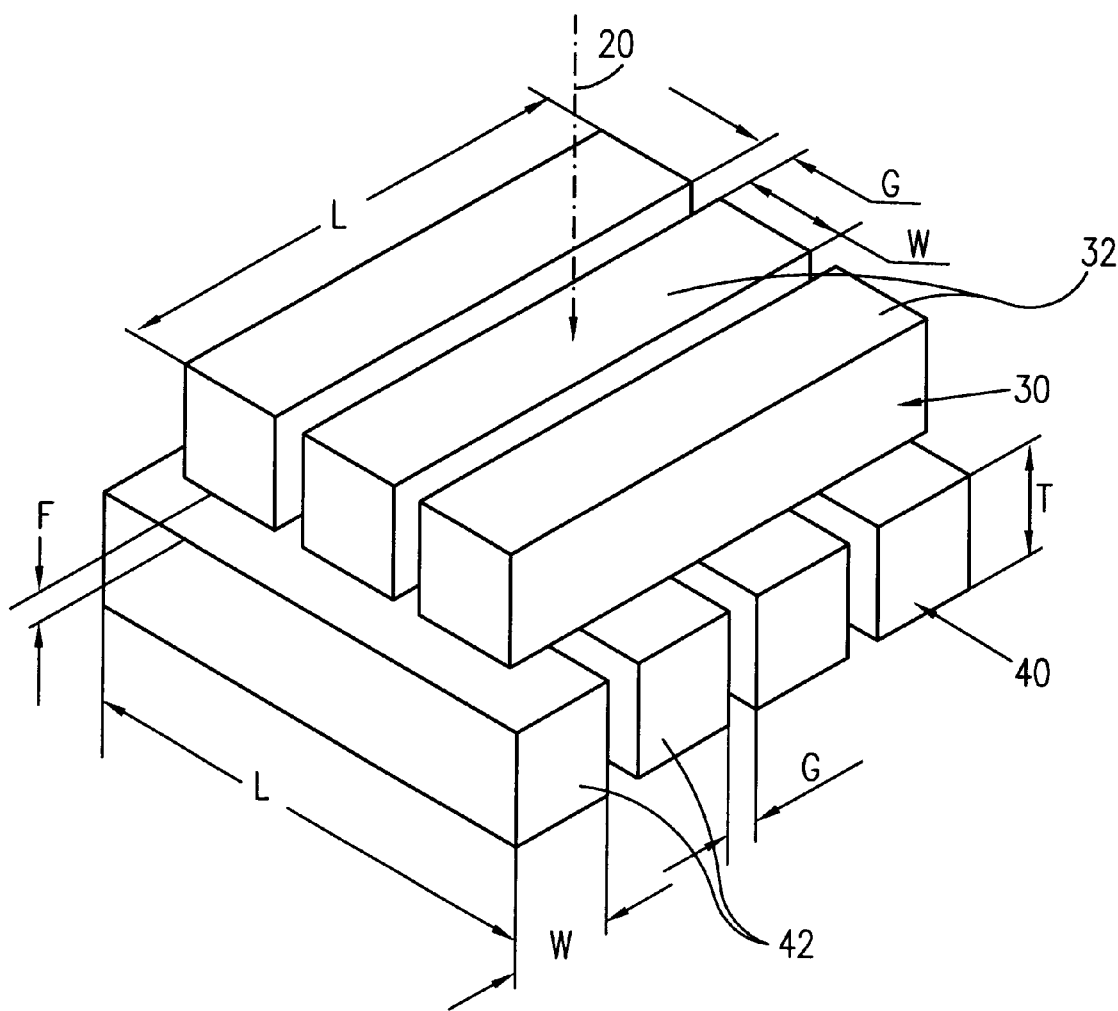
FIG. 4 is a simplified pictorial illustration of adjacent radiation blocking leaves of the multileaf collimator of the radiation system of FIG. 1.

Leaves 32 and 42 are constructed of a radiation impervious material, such as tungsten. Referring now to FIG. 4, each of the leaves is characterized by a length L and a width W traverse to the direction of beam 20, and a thickness T generally along the direction of beam 20. Adjacent leaves in each layer 30 and 40 are separated by a spacing G and layers 30 and 40 are separated by a spacing F. All of the above geometric parameters, L, W, T, G and F may be the same or different for each individual leaf or layer. Another advantage of the present invention is that the unique, crossed overlapping of layers 30 and 40 allows employing smaller values of T than prior art systems such as that of U.S. Pat. No. 5,591,983, thereby realizing cost savings in materials and manufacture.

Referring again to FIG. 1, layers 30 and 40 of leaves 32 and 42, respectively, are housed in a frame 50.

Figure 5:
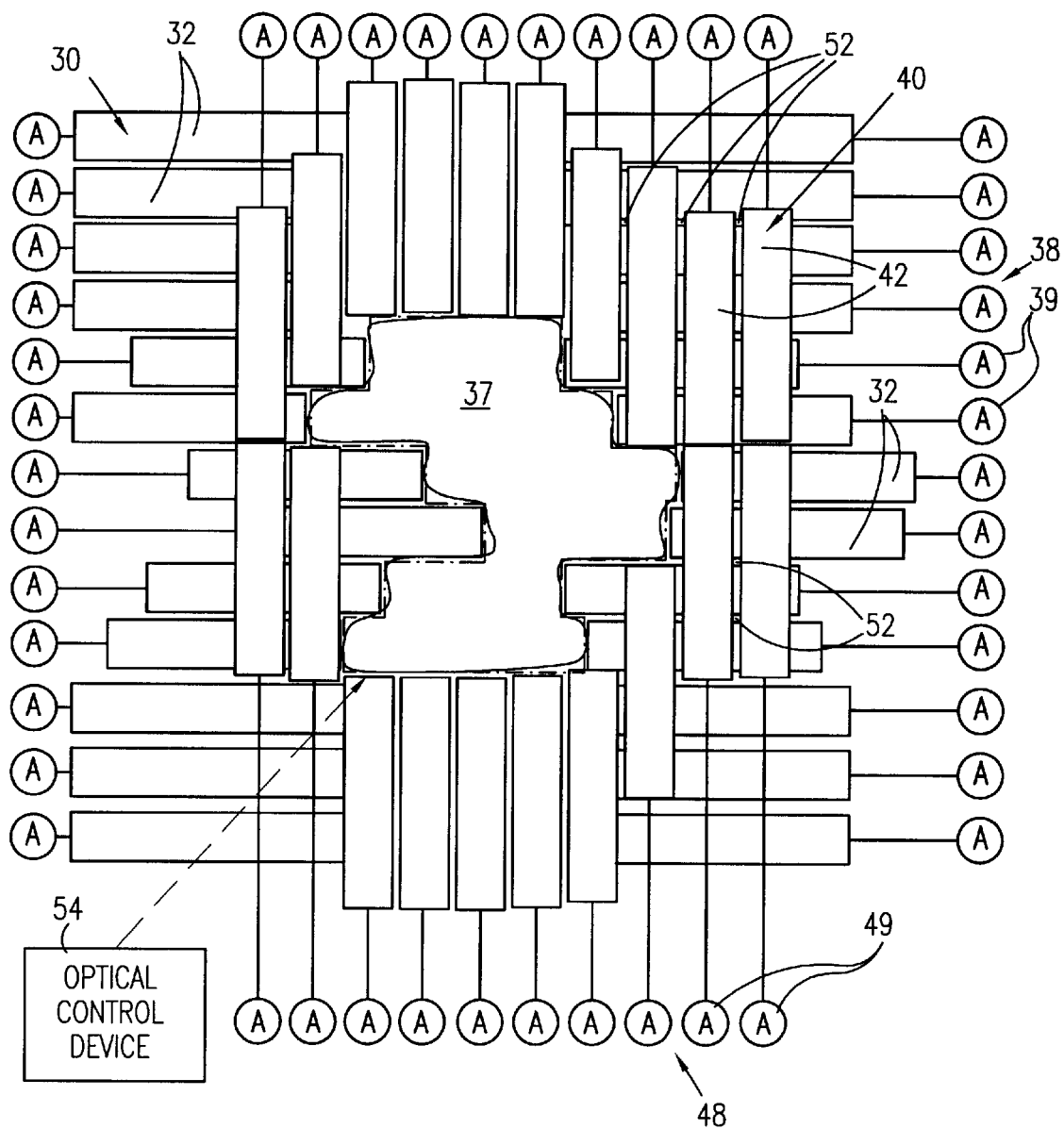
FIG. 5 is a simplified top view illustration of overlapping of the first and second layers in accordance with a preferred embodiment of the present invention, wherein the layers are orthogonal to each other.

Reference is now made to FIG. 5 which is a simplified top view illustration of overlapping of first and second layers 30 and 40 in accordance with a preferred embodiment of the present invention, wherein layers 30 and 40 are orthogonal to each other. It may be seen that the overlapping of layers 30 and 40 helps to improve the resolution of coverage of target 37. Gaps 52 are formed generally traverse to the beam direction 20 and generally in a plane of the X and Y directions, 34 and 44. Each of gaps 52, which may be of equal or varying sizes, only allow an amount of radiation to pass therethrough below a predetermined threshold within the safety standards of the industry. Moreover, if beam 20 is not exactly orthogonal to layers 30 and 40, but rather tilted with respect thereto, even less radiation will pass through gaps 52.

In accordance with a preferred embodiment of the present invention an optical control device 54 is provided that monitors travel of any of the leaves 32 or 42 and signals actuator apparatus 38 and 48, respectively, to stop moving leaves 32 and 42. Optical control device 54 may comprise any suitable optical equipment, such as a camera, CCD or equivalent.

Figure 6:
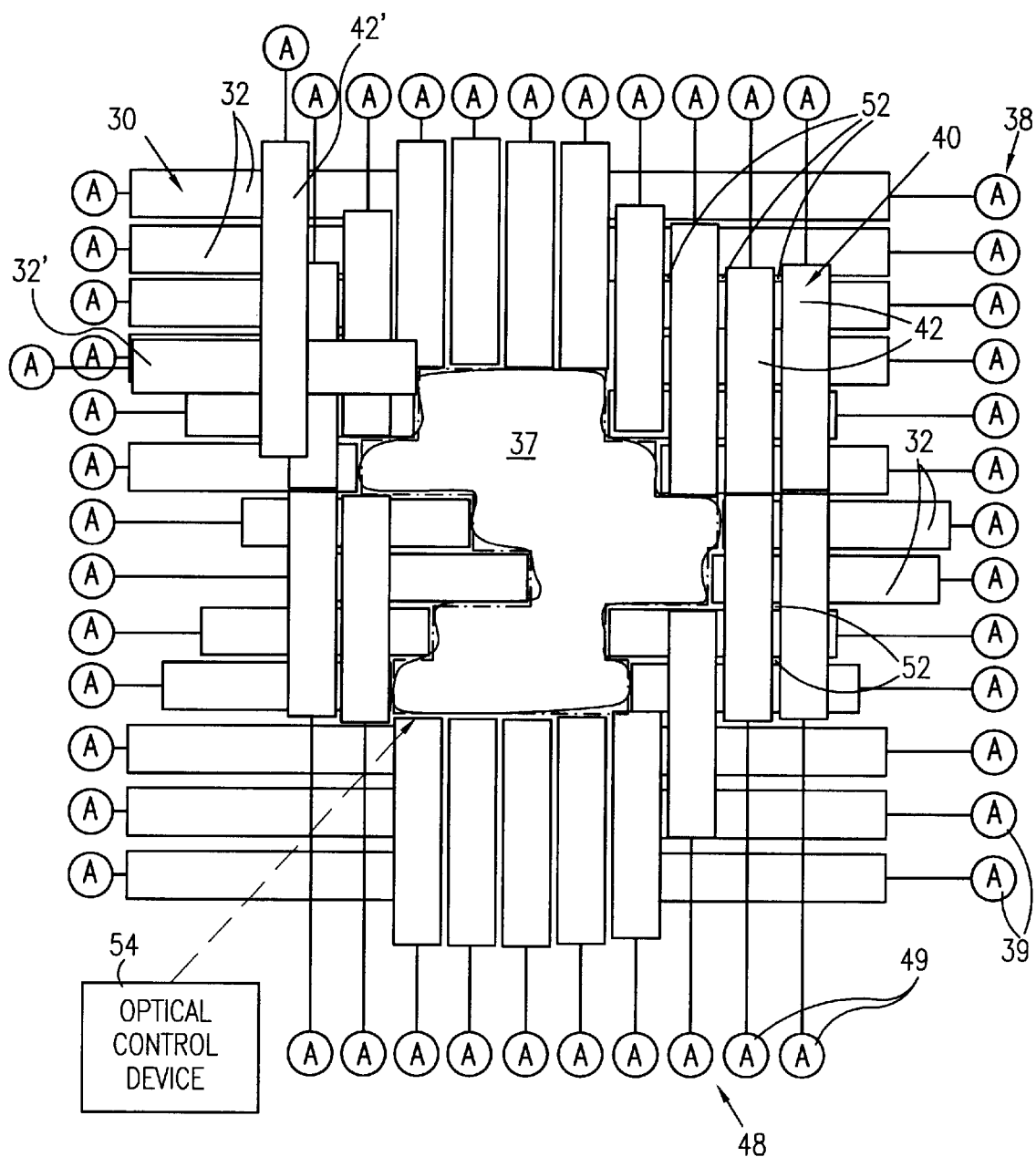
FIG. 6 is a simplified top view illustration of a radiation system constructed and operative in accordance with another preferred embodiment of the present invention, and comprising a plurality of first layers of radiation blocking leaves and a plurality of second layers of radiation blocking leaves.

Reference is now made to FIG. 6 which is a simplified top view illustration of overlapping of first and second layers 30 and 40 in accordance with another preferred embodiment of the present invention. It is seen that the present invention may comprise a plurality of first layers 30 of radiation blocking leaves, only one leaf of an additional layer being shown for the sake of simplicity and designated as leaf 32', and a plurality of second layers 40 of radiation blocking leaves, only one leaf of an additional layer being shown for the sake of simplicity and designated as leaf 42'. As described above, the present invention is not limited to any particular angle between layers 30 and 40.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A multileaf collimator for use in a radiation system providing a radiation beam in a given beam direction, comprising:

a first planar layer of a plurality of radiation blocking leaves, said leaves being arranged adjacent one another so as to form two opposed rows of adjacently positioned leaves and being movable in a longitudinal direction which is generally traverse to the beam direction so as to define a radiation beam shaping field between the opposed ends of the leaves;

a second planar layer of a plurality of radiation blocking leaves, said leaves of said second layer being arranged adjacent one another so as to form two opposed rows of adjacently positioned leaves and being movable in a cross-over direction which is generally traverse to the beam direction and angled with respect to said longitudinal direction so as to define a radiation beam shaping field between the opposed ends of the leaves of said second layer; and actuator apparatus for moving said leaves of said first layer in the longitudinal direction and said leaves of said second layer in the cross-over direction, wherein said first and second layers are arranged one above another in an overlapping manner in the beam direction.

2. The multileaf collimator according to claim 1 and wherein said planar layers are mutually parallel.

3. The multileaf collimator according to claim 1 and wherein gaps are formed generally traverse to the beam direction and generally in a plane of the longitudinal and cross-over directions, each of said gaps only allowing an amount of radiation to pass therethrough below a predetermined threshold.

4. The multileaf collimator according to claim 1 and wherein said cross-over direction is generally orthogonal to said longitudinal direction.

5. The multileaf collimator according to claim 1 and wherein said leaves of said first layer and said leaves of said second layer are housed in a frame.

6. The multileaf collimator according to claim 1 and comprising a source of radiation for providing a radiation beam in said given beam direction.

7. The multileaf collimator according to claim 1 and comprising imaging apparatus for imaging a target irradiated by said radiation beam.

8. The multileaf collimator according to claim 1 and comprising an optical control device that monitors travel of any of the leaves and signals said actuator apparatus to stop moving said leaves.

9. The multileaf collimator according to claim 1 and comprising a plurality of said first layers of radiation blocking leaves.

10. The multileaf collimator according to claim 1 and comprising a plurality of said second layers of radiation blocking leaves.

* * * * *